US009726645B2

(12) United States Patent
Soejima et al.

(10) Patent No.: US 9,726,645 B2
(45) Date of Patent: Aug. 8, 2017

(54) VIBRATION DETECTION APPARATUS AND VIBRATION DETECTION METHOD

(71) Applicants: Fuji Jukogyo Kabushiki Kaisha, Tokyo (JP); The University of Tokyo, Tokyo (JP)

(72) Inventors: Hideki Soejima, Tokyo (JP); Yoji Okabe, Tokyo (JP); Qi Wu, Tokyo (JP)

(73) Assignees: SUBARU CORPORATION, Tokyo (JP); UNIVERSITY OF TOKYO, Tokyo (JP)

( * ) Notice: Subject to any disclaimer, the term of this patent is extended or adjusted under 35 U.S.C. 154(b) by 195 days.

(21) Appl. No.: 14/617,190

(22) Filed: Feb. 9, 2015

(65) Prior Publication Data

US 2015/0247826 A1   Sep. 3, 2015

(30) Foreign Application Priority Data

Feb. 28, 2014 (JP) .................................. 2014-39087

(51) Int. Cl.
 G01H 9/00  (2006.01)
 G01N 29/24 (2006.01)
 G01D 5/353 (2006.01)

(52) U.S. Cl.
CPC ......... *G01N 29/2418* (2013.01); *G01H 9/004* (2013.01); *G01D 5/35316* (2013.01);
(Continued)

(58) Field of Classification Search
CPC ......... G01N 29/2418; G01N 2291/023; G01N 2291/0289; G01N 21/1702;
(Continued)

(56) References Cited

U.S. PATENT DOCUMENTS 4,792,962 A * 12/1988 Miyauchi ................ H01S 3/083
                                                        372/50.1
5,488,475 A    1/1996 Friebele et al.
(Continued)

FOREIGN PATENT DOCUMENTS

| EP | 2 259 037 | 12/2010 |
|---|---|---|
| JP | 2007/232371 | 9/2007 |
| JP | 2011/196744 | 10/2011 |

OTHER PUBLICATIONS

Extended European search report issued Apr. 23, 2015, in Patent Application No. 14 195 846.2 (8 pages).
(Continued)

*Primary Examiner* — Laura Martin
*Assistant Examiner* — Rose M Miller
(74) *Attorney, Agent, or Firm* — Smith, Gambrell & Russell, LLP

(57) ABSTRACT

A vibration detection apparatus includes a ring laser resonator, a fiber Bragg grating and a detection system. The ring laser resonator generates a laser beam propagating a ring shaped optical path. The fiber Bragg grating is disposed in the ring laser resonator such that the laser beam enters the grating, and has a transmittance distribution characteristic of transmitted light in a wavelength direction, which changes in accordance with vibration of an object. The detection system detects the vibration based on the transmitted light through the fiber Bragg grating.

12 Claims, 8 Drawing Sheets

(52) U.S. Cl.
CPC .............. *G01N 2291/023* (2013.01); *G01N 2291/0289* (2013.01)

(58) Field of Classification Search
CPC .. G01N 2021/1708; G01H 9/004; G01H 9/00; G01D 5/35316
USPC .................................. 73/643, 579, 655, 657
See application file for complete search history.

(56) References Cited

U.S. PATENT DOCUMENTS

| | | | | |
|---|---|---|---|---|
| 5,636,021 | A * | 6/1997 | Udd | G01D 5/35383 356/483 |
| 6,122,305 | A | 9/2000 | Putnam et al. | |
| 7,272,160 | B1 * | 9/2007 | Geng | H01S 3/302 372/29.011 |
| 7,283,216 | B1 * | 10/2007 | Geng | G01D 5/35303 356/35.5 |
| 7,470,888 | B2 | 12/2008 | Ogisu et al. | |
| 7,992,440 | B2 * | 8/2011 | Kumagai | G01H 9/004 356/460 |
| 2004/0213501 | A1 | 10/2004 | Chi et al. | |
| 2010/0103426 | A1 | 4/2010 | Kim et al. | |
| 2013/0008253 | A1 | 1/2013 | Tsuda | |
| 2014/0218751 | A1 | 8/2014 | Soejima et al. | |

OTHER PUBLICATIONS

D. Gatti et al: "Fiber strain sensor based on a [pi]-phase-shifted Bragg grating and the Pound-Drever-Hall technique", Optics Express, vol. 16, No. 3, Feb. 4, 2008, p. 1945, XP055182537, ISSN: 1094-4087, DOI: 10.1364/OE.16.001945 (6 pages).
Communication under Rule 71(3) EPC issued on Jul. 6, 2016, European Patent Application No. 14 195 846.2 (8 pages).
Asrul Izam Azmi et al.,"Performance Enhancement of Vibration Sensing Employing Multiple Phase-Shifted Fiber Bragg Grating", Journal of Lightwave Technology, vol. 29, No. 22, Nov. 15, 2011, pp. 3453-3460, XP011391692.
Q. Wu and Y. Okabe, "Ultrasonic sensor employing two cascaded phase-shifted fiber Bragg gratings suitable for multiplexing", Optics Letters., vol. 37, No. 16, pp. 3336-3338, (2012).
Q. Wu and Y. Okabe, "High-sensitivity ultrasonic phase-shifted fiber Bragg grating balanced sensing system", Optics Express., vol. 20, No. 27, pp. 28353-28362, (2012).
Q. Wu and Y. Okabe, "Novel real-time acousto-ultrasonic sensors using the two phase-shifted fiber Bragg gratings", Journal of Intelligent Material Systems and Structures, vol. 25(5) 640-646 / online version., DOI: 10.1177/1045389X13483028, (2013).
Q. Wu, Y. Okabe, K. Saito, and F. Yu, "Sensitivity distribution properties of a phase-shifted fiber Bragg grating sensor to ultrasonic waves", Sensors., 14, pp. 1094-1105, (2014).
Q. Wu and Y. Okabe, "Novel real-time acousto-ultrasonic sensor system using two phase-shifted FBGs", Advances in Structural Health Management and Composite Structures 2012 (ASHMCS 2012), vol. I, p. 09-1, Jeonju, Republic of Korea (2012).
Q. Wu and Y. Okabe, "Novel acoustic emission sensor system based on two cascaded phase-shifted fiber Bragg gratings", $22^{nd}$ International Conference on Optical Fiber Sensors (OFS2012), Beijing, China, Proc. of SPIE., vol. 8421, 84214H-1 (2012).
Q. Wu, F. Yu, K. Saito, Y. Okabe, and S. Kobayashi, "Phase-shifted Fiber Bragg Grating Balanced Sensing System for Detection of Acoustic Emission", $3^{rd}$ International Symposium on Laser Ultrasonics and Advanced Sensing 53, Yokohama, Japan (2013).
F. Yu, Q. Wu, S. Kobayashi, K. Saito, and Y. Okabe, "Application of a Novel Optical Fiber Sensing System to Acoustic Emission Detection in CFRP Laminates", $3^{rd}$ International Symposium on Laser Ultrasonics and Advanced Sensing, 93, Yokohama, Japan (2013).
Q. Wu, Y. Okabe, F. Yu, and K. Saito, "Ultrasensitive Optical-Fiber Ultrasonic Sensor Based on Phase-Shifted Fiber Bragg Gratings", the $9^{th}$ International Workshop on Structurai Health Monitoring, 2063, Stanford, USA (2013).
Q. Wu, F. Yu, and Y. Okabe, "High sensitive optical sensing system based on phase-shifted FBG to detect AE signals and impacts in CFRP laminates", the $37^{th}$ Symposium on Composite Materials, 105-106, Nagoya, Japan (2012).
Q. Wu, F. Yu, Y. Okabe, and K. Saito, "High sensitive PS-FBG ultrasonic sensor for SHM of composite materials", the $4^{th}$ Japan Joint Conference on Composite Materials (JCCM-4), 2A-12, Tokyo, Japan (2013).
Q. Wu, F. Yu, Y. Okabe, K. Saito, and S. Kobayashi, "Acoustic emission detection in CFRP cross-ply laminates by novel PS-FBG optical fiber ultrasonic sensor", the $38^{the}$ Symposium on Composite Materials, A1-1-4, 17, Kagoshima, Japan (2013).
Q. Wu, F. Yu, Y. Okabe, S. Kobayashi, and K. Saito, "AE detection in CFRP composites by a novel optical fiber sensor", the Japan Society of Mechanical Engineers, the $21^{st}$ conference on materials and processing, Tokyo, Japan, 311 (2013).
F. Yu, Q. Wu, Y. Okabe, S. Kobayashi, and K. Saito, "Evaluation of AE signals detected by an optical fiber sensor to identify the damage in composites", the Japan Society of Mechanical Engineers, the $21^{st}$ conference on materials and processing, Tokyo, Japan, 323 (2013).
F. Yu, Y. Okabe, Q. Wu, S. Kobayashi, and K. Saito, "Identification of damage types in CFRP laminates from AE signals detected by a new optical fiber sensor", the $21^{st}$ Symposium on Non-Destructive Inspection by ultrasonic, Tokyo, Japan, 11-14 (2014).
H. Tsuda, "Fiber Bragg grating vibration-sensing system, insensitive to Bragg wavelength and employing fiber ring laser", Optics Letters vol. 35, No. 14, pp. 2349-2351, (2010).
M. Han, T. Liu, L. Hu, and Q. Zhang, "Intensity-demodulated fiber-ring laser sensor system for acoustic emission detection", Optics Express., vol. 21 No. 24, 29269-29276 (2013).

* cited by examiner

VIBRATION DETECTION APPARATUS AND VIBRATION DETECTION METHOD

CROSS-REFERENCE TO RELATED APPLICATIONS

The present application claims priority from Japanese Patent Application No. 2014-039087 filed on Feb. 28, 2014, the entire contents of which are hereby incorporated by reference.

BACKGROUND

1. Technical Field

The implementation of the present invention relates to a vibration detection apparatus and a vibration detection method.

2. Related Art

A technique to detect vibration, such as ultrasonic vibration, using a fiber Bragg grating (FBG) or arrayed waveguide grating (AWG), has been known (e.g. see Japanese Unexamined Patent Application Nos. 2011-196744 and 2007-232371).

SUMMARY OF THE INVENTION

An object of the present invention is to provide a vibration detection apparatus and a vibration detection method that allow detecting a vibration, an ultrasound, an acoustic emission (AE) or the like, with a good Signal-to-Noise-Ratio (SNR).

An aspect of the present invention provides a vibration detection apparatus including a ring laser resonator, a fiber Bragg grating and a detection system. The ring laser resonator generates a laser beam propagating a ring-shaped light path. The fiber Bragg grating is disposed in the ring laser resonator such that the laser beam enters the grating, and has a transmittance distribution characteristic of transmitted light in a wavelength direction, which changes in accordance with vibration of an object. The detection system detects the vibration based on the transmitted light through the fiber Bragg grating.

Another aspect of the present invention provides a vibration detection method including a step of generating a laser beam propagating a ring-shaped light path, a step of allowing the laser beam to enter a fiber Bragg grating of which transmittance distribution characteristic of transmitted light in a wavelength direction changes in accordance with vibration of an object, and a step of detecting the vibration based on the transmitted light through the fiber Bragg grating.

DETAILED DESCRIPTION

A vibration detection apparatus and a vibration detection method according to an implementation of the present invention will be described with reference to the accompanying drawings.

(Configuration and Functions)

Figure 1:
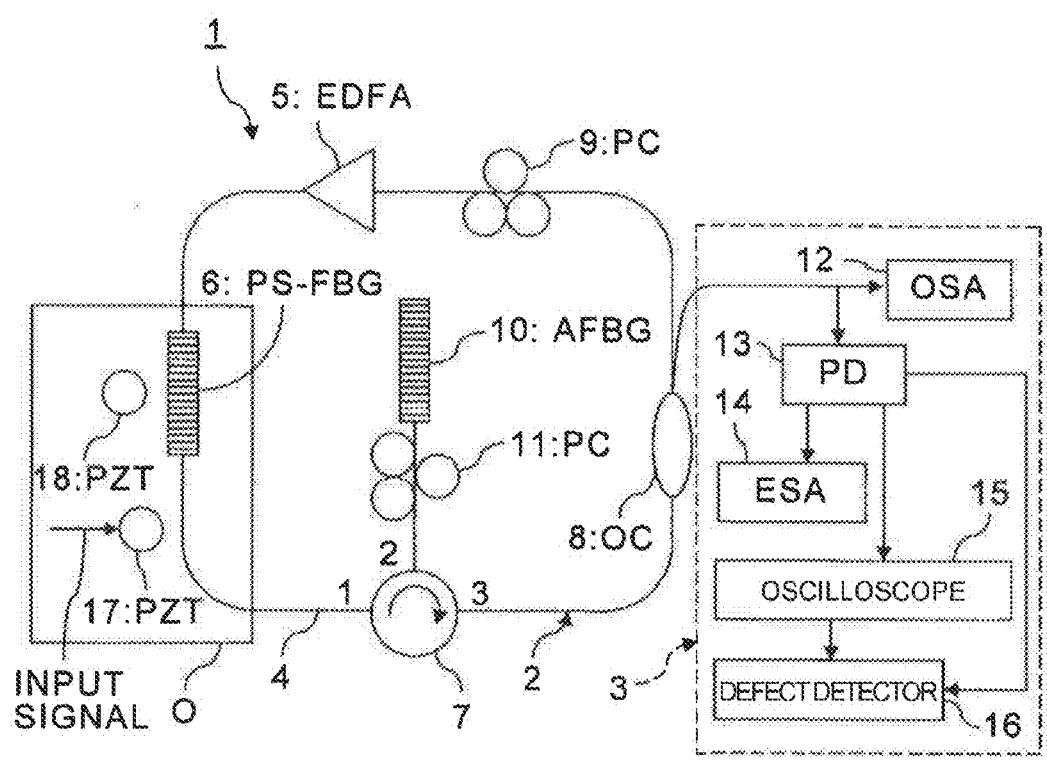
FIG. 1 is a block diagram depicting a vibration detection apparatus according to an implementation of the present invention.

FIG. 1 is a block diagram of the vibration detection apparatus 1 according to an implementation of the present invention.

The vibration detection apparatus 1 is a system that detects the vibration generated in an object O constituted by such a metal as aluminum or such a mixed material as carbon fiber reinforced plastic (CFRP). To activate this function, the vibration detection apparatus 1 includes an optical system 2 and a detection system 3.

The optical system 2 can be configured by connecting an optical fiber amplifier 5, an FBG 6, an optical circulator 7, an optical coupler (OC) 8 and a first polarization controller (PC) 9 to a ring-shaped optical fiber 4. A reflection type optical filter 10 is connected to an edge of an optical fiber, which is branched from the ring-shaped optical fiber 4 via the optical circulator 7. In other words, it is preferable that the optical filter 10 is connected to the ring-shaped optical fiber 4 via the optical circulator 7. If necessary, a second PC 11 is also connected between the optical circulator 7 and the optical filter 10.

For the ring-shaped optical fiber 4, a single mode optical fiber that transmits light in a single mode, for example, can be used. The ring-shaped optical fiber 4 functions as the ring laser resonator of the present invention, which generates an amplified laser beam propagating a ring-shaped light path.

If the laser beam enters the ring-shaped optical fiber 4 that functions as a ring resonator, a plurality of longitudinal modes, in accordance with the resonance frequency of the ring resonator, is generated discontinuously by the resonance phenomena of the laser beam. The longitudinal mode is a mode of an electromagnetic field in the optical axis direction (light propagation direction), and corresponds to a plurality of linear spectra in a wavelength direction of which half value width is extremely narrow. Particularly in the ring laser resonator, many longitudinal modes are generated.

A typical example of the optical fiber amplifier 5 is an erbium doped fiber amplifier (EDFA), as illustrated in FIG. 1. EDFA is the optical fiber amplifier 5 created by injecting erbium ions into the core of an optical fiber.

The FBG 6 is disposed on the ring-shaped optical fiber 4 functioning as a ring laser resonator, so that a strong laser beam enters the FBG 6. The FBG 6 is ideally constituted by a phase-shifted FBG (PS-FBG). The PS-FBG is an FBG in which a phase shift is locally used for the periodic fluctuation of the refractive index. For example, the PS-FBG can be created by connecting two FBGs of which phases for periodic fluctuation of the refractive index are shifted from each other by 180°.

The spectrum of the transmitted light through the PS-FBG in the wavelength domain is a spectrum of which bandwidth is extremely narrow and the slope is sharp. Therefore if the PS-FBG is used as the FBG 6, only a specific longitudinal mode, out of a plurality of longitudinal modes generated by the resonance of the laser beam that propagates through the ring-shaped optical fiber 4, can be transmitted. In other words, the PS-FBG functions as an optical filter element to extract a specific longitudinal mode from a plurality of longitudinal modes.

The FBG 6 is attached to the object O so as to vibrate as the object O vibrates. For example, the FBG 6 can be contacted to the object O using an ultrasonic couplant having high acoustic impedance. Then if the object O is vibrated by an ultrasonic wave or AE, the vibration propagates to the FBG 6.

When vibration is applied to the object O and the object O is displaced by strain, the FBG 6, to which the vibration propagates, stretches along with the object O. If the FBG 6 is stretched, the Bragg wavelength of the FBG 6 shifts. As a result, the wavelength spectrum of the transmitted light through the FBG 6 changes in the wavelength direction in accordance with the stretching amount of the FBG 6. In other words, the wavelength spectrum of the transmitted light through the FBG 6 changes in the wavelength direction by a shift amount in accordance with the amplitude of the vibration of the object O. This means that the transmittance distribution characteristic of the transmitted light through the FBG 6 in the wavelength direction changes in accordance with the vibration of the object O.

Therefore the intensity of the longitudinal mode that is transmitted through the FBG 6 changes by the amount in accordance with the intensity of the vibration of the object O. This means that the vibration of the object O can be detected by observing the temporal change of the intensity of the longitudinal mode transmitted through the FBG 6. Thus, it is preferable that the FBG 6, constituted by the PS-FBG, has a function of the optical sensor for detecting the vibration of the object O, in addition to the function as an optical filter element that selects a specific longitudinal mode from a plurality of longitudinal modes generated by the resonance of the laser beam. Hence, in the case of applying the ultrasonic vibration to the object O, the FBG 6 can be used as an ultrasonic reception sensor.

The incident light to the FBG 6 is generated by the optical fiber amplifier 5. The transmitted light through the FBG 6 propagates the ring-shaped optical fiber 4, and is amplified by the optical fiber amplifier 5. Then the transmitted light through the FBG 6, amplified by the optical fiber amplifier 5, propagates the ring-shaped optical fiber 4 again, and enters the FBG 6. In this way, the optical fiber amplifier 5 plays a role of amplifying the transmitted light through the FBG 6 having a wavelength spectrum in accordance with the vibration of the object O, generated by the light entering the FBG 6, and allows the transmitted light to enter the FBG 6 again.

The optical circulator 7 is an optical element that emits a laser beam that enters from the ring-shaped optical fiber 4 toward the optical filter 10, and passes the laser beam reflected in the optical filter 10 back to the ring-shaped optical fiber 4.

The OC 8 is an optical element that branches a part of the laser beam that entered from the ring-shaped optical fiber 4. The laser beam branched by the OC 8 is outputted to the detection system 3 as detection light.

The first PC 9 and the second PC 11 are optical elements that control the polarization state of the laser beam respectively. In concrete terms, the polarization state is controlled so that the directivity of the laser beam is improved by the first PC 9 and the second PC 11.

The optical filter 10 is an optical element that removes the components in an unnecessary wavelength band from the transmitted light passing through the FBG 6. The optical filter 10 can be constituted by a reflection type apodized FBG (AFBG), as illustrated. The AFBG is an FBG in which the side lobe that appears in the wavelength spectrum of transmitted light or reflected light is suppressed.

If an AFBG is used for the optical filter 10, a clear optical signal can be acquired. This allows using the clear transmitted light through the FBG 6 as the incident light for the next FBG 6.

Figure 2:
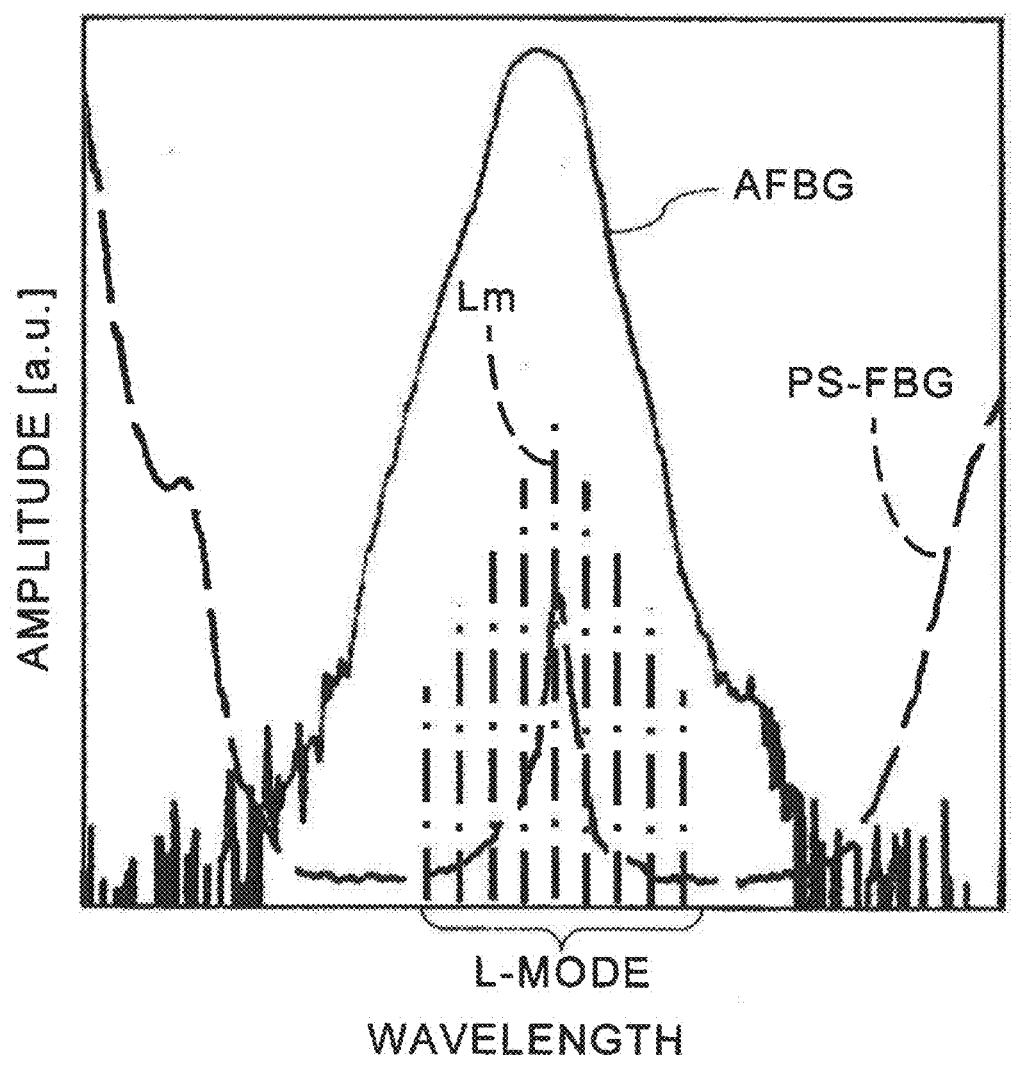
FIG. 2 is a diagram illustrating an example of a wavelength spectrum of transmitted light through a PS-FBG used as the FBG in FIG. 1, and a wavelength spectrum of reflected light of an AFBG used as the optical filter in FIG. 1.

FIG. 2 is a diagram illustrating an example of a wavelength spectrum of transmitted light passing through the PS-FBG used as the FBG 6 in FIG. 1, and a wavelength spectrum of reflected light from the AFBG used as the optical filter 10 in FIG. 1.

In FIG. 2, the abscissa indicates the wavelength of the light, and the ordinate indicates the intensity of the light. The broken line in FIG. 2 indicates a transmission spectrum of the PS-FBG, and the solid line indicates the reflection spectrum of the AFBG. As illustrated in FIG. 2, the transmission spectrum of the PS-FBG has a peak having an extremely narrow band. If the Bragg wavelength of the AFBG having the reflection spectrum of which band is wider than the PS-FBG is converted into an equivalent Bragg wavelength of the PS-FBG, then the peak of the reflection spectrum of the AFBG covers the peak of the transmission spectrum of the PS-FBG, as illustrated in FIG. 2.

Therefore the transmitted light of the PS-FBG in the wavelength band that corresponds to the central wavelength of the transmission spectrum of the PS-FBG is reflected in the AFBG. On the other hand, unnecessary long wavelength components and short wavelength components, which as transmitted through the PS-FBG, are outside the wavelength band of the reflection spectrum of the AFBG. Hence the AFBG can remove the unnecessary wavelength components from the transmitted light through the PS-FBG. In other words, the laser beam that is transmitted through the PS-FBG and is reflected by the AFBG is a laser beam that has a wavelength in the peak wavelength band of the transmission spectrum of the PS-FBG. By combining the PS-FBG and the AFBG in this manner, an optical filter having an extremely narrow bandwidth, and which is used for detecting a laser beam having a specific wavelength, can be created.

On the other hand, a plurality of longitudinal modes (L-modes) indicated by the dashed line in FIG. 2 is generated in the wavelength direction by the resonance of the laser beam that propagates through the ring-shaped optical fiber 4 having a long optical path length. The plurality of longitudinal modes enters the PS-FBG, but the longitudinal mode that is transmitted through the PS-FBG becomes the longitudinal mode having a wavelength in the peak wavelength band of the transmission spectrum of the PS-FBG. Therefore a main longitudinal mode Lm, that has a specific amplitude or wavelength, can be selectively transmitted by appropriately adjusting the transmission characteristic of the PS-FBG.

Figure 3:
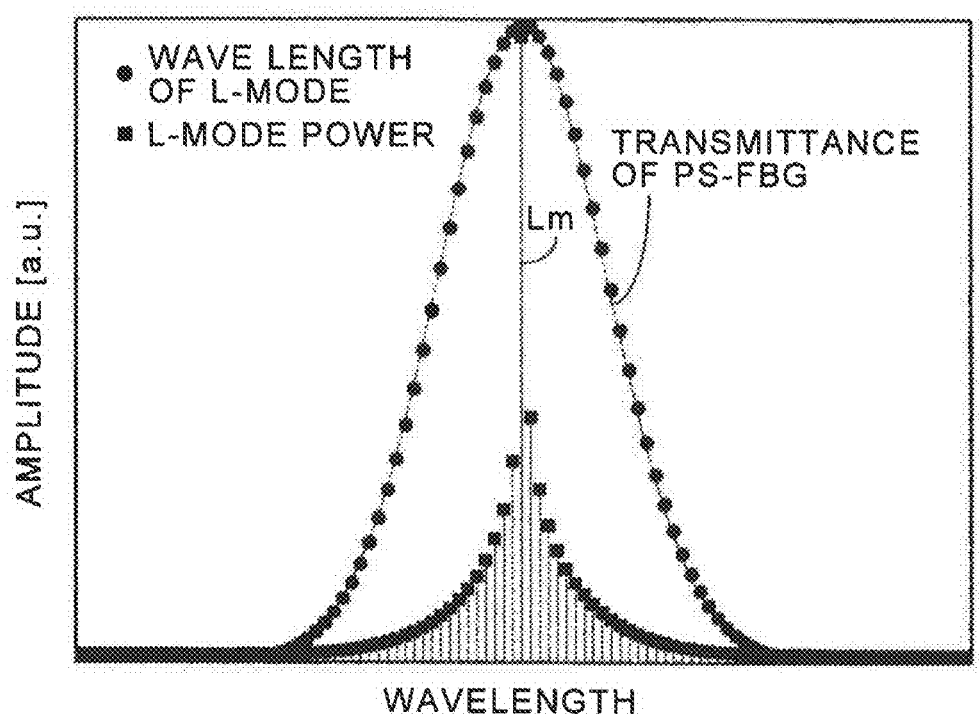
FIG. 3 is a diagram illustrating a simulation result of a main longitudinal mode Lm, which is extracted by the PS-FBG having the transmission spectrum illustrated in FIG. 2.

FIG. 3 is a diagram illustrating a simulation result of a main longitudinal mode Lm, which is extracted by the PS-FBG having a transmission spectrum illustrated in FIG. 2.

In FIG. 3, the abscissa indicates the wavelength of the light, and the ordinate indicates the relative intensity of the light. As illustrated in FIG. 3, many longitudinal modes having different wavelengths are generated by the ring laser resonator. From this, a main longitudinal mode Lm, having a specific wavelength, can be selectively transmitted through the PS-FBG which has a sharp transmission spectrum.

The Bragg wavelength of the PS-FBG changes depending on environmental factors, such as a change in temperature and a change in quasi-static strain. Hence if the Bragg wavelength of the PS-FBG is largely shifted by a dramatic change in temperature or the like, the wavelength of the main longitudinal mode Lm, selected by the PS-FBG, is likely to be outside the band of the transmission spectrum of the PS-FBG. In other words, the wavelength of the main longitudinal mode Lm is likely to be outside the measurement range. In the ring-shaped optical fiber 4, however, a plurality of longitudinal modes is generated, as illustrated in FIG. 2. Therefore the measurement range can be self-adjusted in the wavelength direction of the laser beam using the PS-FBG.

Figure 4:
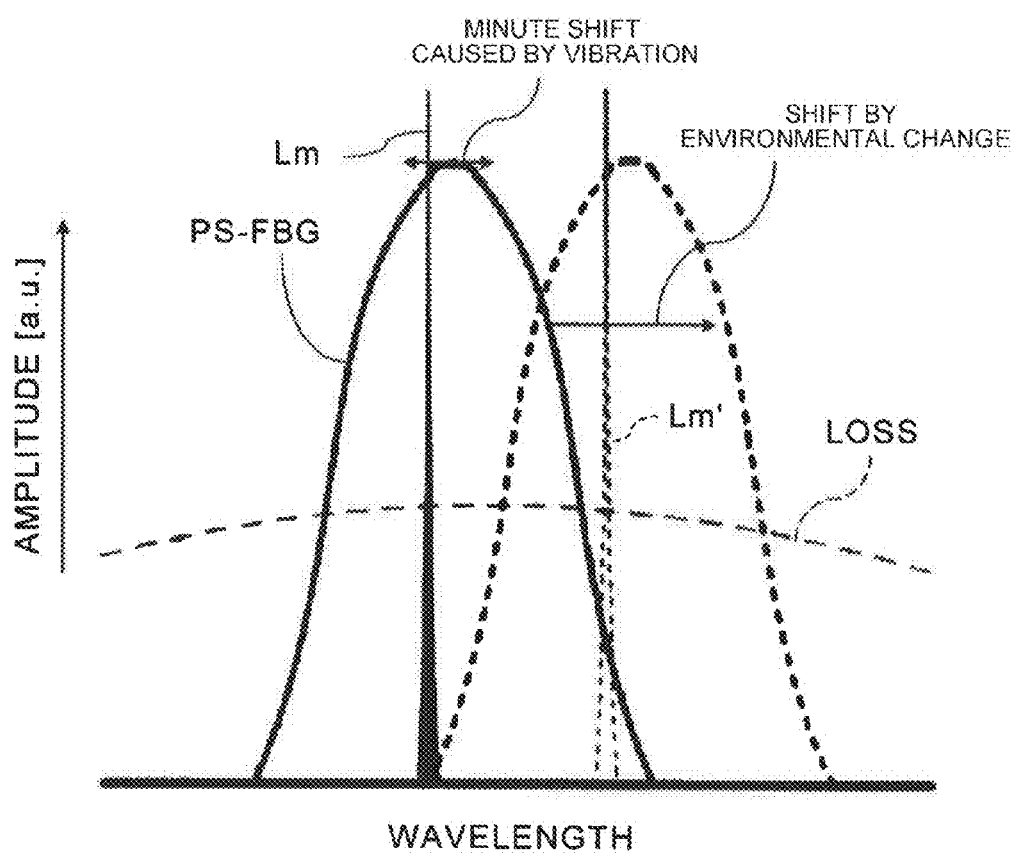
FIG. 4 is a diagram depicting a self adjustment function for a laser beam measurement range in PS-FBG.

FIG. 4 is a diagram depicting a self adjustment function for a laser beam measurement range in the PS-FBG.

In FIG. 4, the abscissa indicates the wavelength, and the ordinate indicates the relative intensity. The solid lines in FIG. 4 indicate the transmission spectrum of the PS-FBG and the main longitudinal mode Lm that is transmitted through the PS-FBG corresponding to the transmission spectrum. The broken line indicates the optical loss.

When vibration is applied to the PS-FBG, the transmission spectrum of the PS-FBG is slightly shifted in the wavelength direction. However if a major change occurs to an environmental factor, such as temperature, the transmission spectrum of the PS-FBG is largely shifted to the wavelength direction. As a result, the transmission spectrum of the PS-FBG becomes the spectrum indicated by the dotted line.

Then the main longitudinal mode that is transmitted through the PS-FBG becomes a longitudinal mode Lm', which is adjacent to the main longitudinal mode Lm that has been transmitted through the PS-FBG before the shift caused by the change of an environmental factor. In other words, the laser beam has a wavelength of which the main longitudinal mode that is transmitted through the PS-FBG is different. This means that even if an environmental factor, such as temperature, in the location where the PS-FBG is disposed, changes, the wavelength of the main longitudinal mode that is transmitted through the PS-FBG is self-adjusted, and the strong laser is always transmitted through the PS-FBG.

If the detection light is generated like this by the method of selecting a main longitudinal mode having a specific wavelength from a plurality of longitudinal modes having different wavelengths using the PS-FBG, a sensor that can track an environmental change, such as a temperature change, can be created.

Figure 5A:
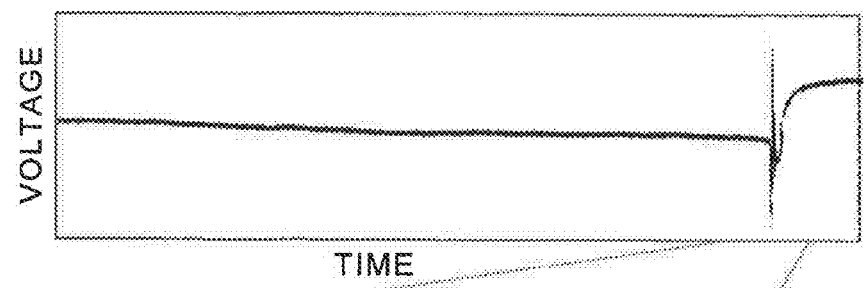
FIGS. 5A to 5C are diagrams illustrating an example when the self adjustment for the measurement range is generated in the PS-FBG.
Figure 5B:
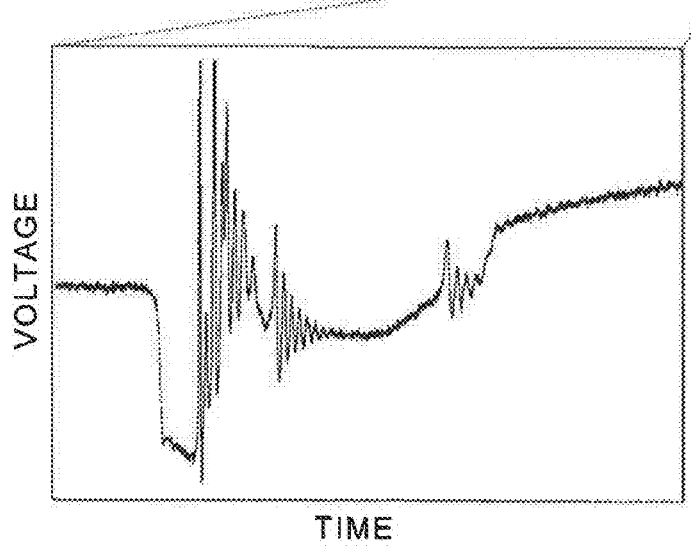
Figure 5C:
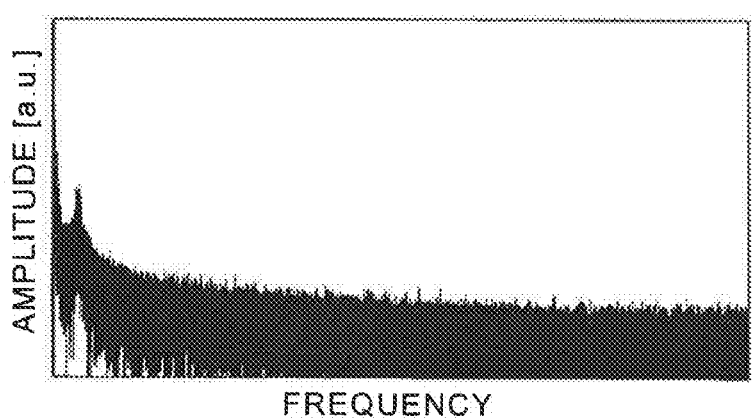

FIGS. 5A to 5C are diagrams illustrating an example when self adjustment for the measurement range is generated in the PS-FBG.

In FIG. 5A and FIG. 5B, each abscissa indicates the time, and each ordinate indicates the relative voltage of a DC electric signal that corresponds to the intensity of the main longitudinal mode that is transmitted through the PS-FBG. In FIG. 5C, the abscissa indicates the frequency of the electric signal in FIGS. 5A and 5B, and the ordinate indicates the relative intensity of the electric signal in FIGS. 5A and 5B.

FIG. 5A illustrates a change in the voltage of the electric signal that corresponds to the transmission light through the PS-FBG when the temperature change temporally. As illustrated in FIG. 5A, the intensity of the main longitudinal mode that is transmitted through the PS-FBG stably and gradually drops in an approximate linear manner in accordance with the temperature change. This is probably because the transmission spectrum of the PS-FBG gradually shifts in the wavelength direction and optical loss increases in accordance with the temperature change.

If the temperature change amount exceeds the threshold, the intensity of the main longitudinal mode that is transmitted through the PS-FBG suddenly changes. This is because the transmission spectrum of the FBG largely shifted in the wavelength direction by the temperature change, and the main longitudinal mode to be the measurement target of the intensity shifted to the adjacent longitudinal mode.

FIG. 5B is an enlarged view of the discontinuous portion of the electric signal illustrated in FIG. 5A. As illustrated in FIG. 5A and FIG. 5B, the amplitude of the main longitudinal mode can be stably measured by the self-adjustment of the wavelength of the longitudinal mode that is transmitted through the PS-FBG, even if the temperature changes considerably. In other words, the amplitude of the main longitudinal mode can be stably measured without performing feedback control for adjusting the narrow dynamic range of the PS-FBG.

FIG. 5C illustrates the result of the fast Fourier transform (FFT) of the portion in FIG. 5A in the state when the electric signal is stable. According to FIG. 5C, a peak appears in the low frequency region due to the relaxation oscillation of the laser beam.

The main longitudinal mode Lm, which has been transmitted through the PS-FBG and reflected by the AFBG, can be amplified as described above, by the resonance of the optical fiber amplifier 5 and the ring laser. The amplified main longitudinal mode Lm enters the PS-FBG again. As a consequence, the amplitude of the main longitudinal mode Lm can be amplified to a predetermined amplitude by repeating the amplification of the main longitudinal mode Lm a plurality of times.

The detection system 3 is a system that detects the vibration of the object O based on the transmitted light through the FBG 6, which has been amplified by the optical fiber amplifier 5 at least once, and of which intensity has reached a predetermined intensity. Therefore the detection system 3 is connected to the output side of the optical fiber, which branches from the ring-shaped optical fiber 4 via the OC 8.

To detect the vibration of the object O, it is preferable, in terms of improving the sensitivity and the accuracy, to refer to the amplitude of the main longitudinal mode Lm extracted by the PS-FBG, as in the example mentioned above. In other words, the vibration of the object O can be detected based on the change of the intensity of the longitudinal mode Lm having the highest intensity that is transmitted through the PS-FBG, out of a plurality of longitudinal modes generated in the ring-shaped optical fiber 4. If the transmittance distribution characteristic of the PS-FBG is shifted in the wavelength direction by a shift amount exceeding the threshold due to an environmental factor (e.g. temperature) other than the vibration of the object O, the vibration of the object O is detected based on the change of the intensity of another longitudinal mode that corresponds to the shift amount.

In this case, the amplitude of the main longitudinal mode Lm is changed by a subtle shift in the transmittance spectrum of the PS-FBG in the wavelength direction due to the vibration of the object O. Therefore the temporal change in the amplitude of the main longitudinal mode Lm corresponds to the vibration waveform of the object O. As a result, the vibration of the object O can be detected as the temporal change of the amplitude of the main longitudinal mode Lm. Further, a table or functions to indicate the relationship between the amplitude of the vibration of the object O and the amplitude of the main longitudinal mode Lm may be provided in advance, so that the temporal change of the amplitude of the main longitudinal mode Lm is converted into the vibration waveform of the object O.

For example, the detection system 3 may be configured by an optical spectrum analyzer (OSA) 12, a photo detector (PD) 13, an electrical spectrum analyzer (ESA) 14, an oscilloscope 15, and a defect detector 16. In concrete terms, the optical transmission line may be configured such that the detection light outputted from the OC 8 to the detection system 3 is inputted to one or both of the OSA 12 and the PD 13. The detection light detected by the PD 13 is converted into an electric signal having an amplitude waveform that corresponds to the amplitude waveform of the detection light, and is outputted to the ESA 14, the oscilloscope 15 and the defect detector 16 respectively.

The OSA 12 is used to optically observe the wavelength spectrum of the detection light. In other words, a two-dimensional graph of which abscissa is the wavelength and the ordinate is the intensity of the detection light is displayed on the screen of the OSA 12. The ESA 14, on the other hand, is used to observe the frequency spectrum of the electric signal that corresponds to the detection light. In other words, a two-dimensional graph of which abscissa is the frequency and the ordinate is the intensity of the electric signal that corresponds to the detection light is displayed on the screen of the ESA 14.

The oscilloscope 15 is used to observe the temporal change of the intensity of the electric signal that corresponds to the detection light. In other words, the two-dimensional graph of which abscissa is the time and the ordinate is the intensity of the electric signal that corresponds to the detection light is displayed on the screen of the oscilloscope 15. Here the temporal change of the amplitude of the transmitted light, such as the main longitudinal mode Lm, through the FBG 6, can be observed.

The temporal change of the amplitude of the transmitted light, such as the main longitudinal mode Lm, through the FBG 6, indicates that the object O vibrated as mentioned above. Therefore in the oscilloscope 15, the vibration of the object O, due to such ultrasonic waves as an ultrasonic lamb wave or the vibration due to the AE generated in the object O, can be detected.

The defect detector 16 can detect a defect in the object O. The defect of the object O can be detected based on the vibration detected using the oscilloscope 15 or by the amplitude waveform of the detection light.

For example, the waveform pattern of the detection light when the ultrasonic vibration is applied to a non-defective object O can be stored in advance. Then it can be detected that the object O is defective when a minimum square error or a divergence of cross-correlation functions between the observed waveform pattern of the detection light and the stored waveform pattern of the detection light exceeds a predetermined threshold. Instead, it may be detected that the object O is defective when the vibration by AE is detected.

Beside these composing elements, the vibration detection apparatus 1 may include an ultrasonic wave transmission system 17 and an ultrasonic wave reception system 18 as additional composing elements. The ultrasonic wave transmission system 17 is a system to apply the ultrasonic vibration to the object O. The ultrasonic wave reception system 18, on the other hand, is a system to receive the ultrasonic vibration that propagates through the object O. The ultrasonic wave transmission system 17 and the ultrasonic wave reception system 18 can be piezoelectric elements constituted by lead zirconate titanate (PZT) or the like.

If the ultrasonic wave transmission system 17 is disposed in the vibration detection apparatus 1, the vibration detection apparatus 1 can be used as an ultrasonic flaw detection device, which applies ultrasonic vibration to the object O, and detects whether a defect exists. If the ultrasonic wave reception system 18 is disposed in the vibration detection apparatus 1, the optical system 2 and the detection system 3 can be calibrated by comparing the ultrasonic waveform received by the ultrasonic wave reception system 18 and the ultrasonic waveform optically detected as the amplitude waveform of the detection light by the detection system 3.

(Operation and Function)

The operation and function of the vibration detection apparatus 1 will be described next.

When non-destructive flaw detection inspection is performed using the vibration detection apparatus 1, an ultrasonic vibration is applied to the object O from the ultrasonic wave transmission system 17. Because of this, the ultrasonic vibration propagates from the object O to the FBG 6, such as a PS-FBG, disposed on the ring-shaped optical fiber 4. Then the transmittance distribution characteristic of the transmitted light through the FBG 6 in the wavelength direction changes in accordance with the vibration waveform of the object O. This is also the same when the vibration generated by the AE propagates to the object O.

On the other hand, the laser beam enters the FBG 6 from the optical fiber amplifier 5. Thereby the transmitted light of the FBG 6 having a wavelength spectrum in accordance with the vibration waveform of the object O, generated by the entry of light into the FBG 6, is emitted from the FBG 6. The transmitted light emitted from the FBG 6 enters the optical filter 10, constituted by the AFBG or the like, via the optical circulator 7. As a result, the reflected light from the optical filter 10, generated from the transmitted light through the FBG 6, enters the ring-shaped optical fiber 4 via the optical circulator 7.

Therefore the transmitted light through the FBG 6 after the noise components are removed enters the optical fiber amplifier 5 and is amplified. The transmitted light through the FBG 6, that is amplified by the optical fiber amplifier 5, enters the FBG 6 again. Then removal of the noise components from the transmitted light through the FBG 6 and amplification of the transmitted light through the FBG 6 after the noise components are removed are repeated for an appropriate number of times. In concrete terms, the amplification of the transmitted light through the FBG 6 is repeated until the intensity of the transmitted light through the FBG 6 reaches a sufficient intensity.

The transmitted light through the FBG 6, of which intensity has reached a predetermined intensity by amplification one or more times, is outputted to the detection system 3. Then the vibration of the object O is detected using the oscilloscope 15 of the detection system 3 based on the transmitted light through the FBG 6. In particular, when the PS-FBG is used as the FBG 6, the main longitudinal mode can be extracted as the transmitted light through the PS-FBG. This means that the vibration of the object O can be detected as a temporal change of the amplitude of the main longitudinal mode due to a shift in the transmission spectrum of the PS-FBG. In the OSA 12, the transmission spectrum of the FBG 6 can be observed.

The defect detector 16 determines whether the object O is defective based on the wave pattern of the vibration detected in the oscilloscope 15, or on the vibration of the transmitted light through the FBG 6. For example, a defect can be detected based on the difference between the ultrasonic vibration applied to the object O and the ultrasonic vibration detected in the oscilloscope 15. If a vibration is detected with the oscilloscope 15 when the ultrasonic vibration is not applied to the object O, it is determined that a defect in the object O exists. In this way, the flaw detection inspection can be performed for the object O.

In other words, the above mentioned vibration detection apparatus 1 includes the FBG 6, such as the PS-FBG, as the optical sensor, and the optical filter 10, such as the AFBG, in the ring laser resonator, and the vibration of the object O is measured by observing the amplitude of the main longitudinal mode of the transmitted light through the FBG 6 generated by the ring laser.

(Effects)

Therefore according to the vibration detection apparatus 1, the vibration of the object O can be detected with good SNR. As a result, averaging is unnecessary, and the measurement time and a number of measurement times can be decreased compared with prior arts. Furthermore, the vibration of the object O can be detected with high accuracy. These effects are particularly conspicuous when the PS-FBG is used as the FBG 6, and when the optical filter 10, such as the AFBG, is disposed in the vibration detection apparatus 1.

As a result, even a vibration of which energy level is low, such as a vibration due to AE, generated when a defect is generated inside a composite material used as the material for an aircraft, can be detected.

FIGS. 6A to 6D are diagrams illustrating the comparison between an ultrasonic vibration detected by the vibration detection apparatus 1 in FIG. 1, and a detection result by another detection apparatus.

Figures 6A, 6B, 6C, 6D:
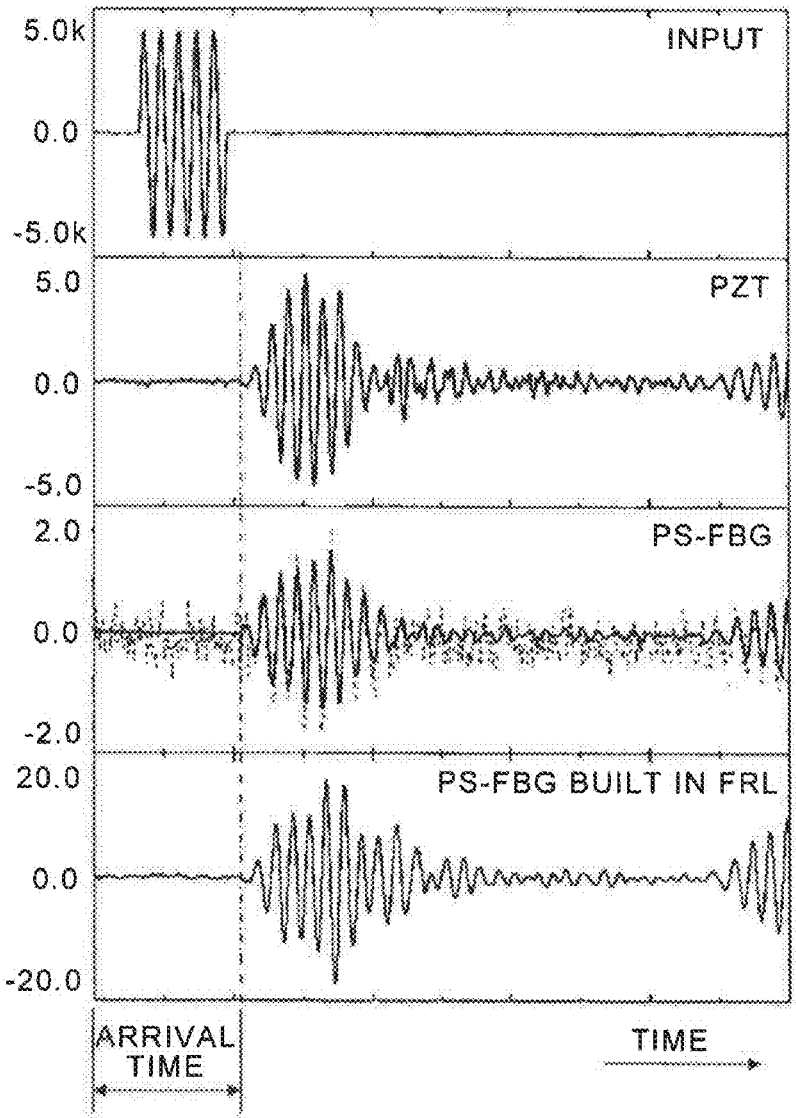
FIGS. 6A to 6D are diagrams illustrating a comparison between an ultrasonic vibration detected by the vibration detection apparatus in FIG. 1 and a detection result by another detection apparatus.

In FIGS. 6A, 6B, 6C and 6D, each abscissa indicates the time, and the ordinate indicates the voltage of an electric signal. FIG. 6A illustrates a voltage waveform of an input signal applied to an ultrasonic vibrator as an AC electric signal for applying the ultrasonic vibration to the object. As illustrated in FIG. 6A, a 5-cycle sinusoidal signal is converted into an ultrasonic signal and transmitted to the object.

FIG. 6B illustrates a voltage waveform of an ultrasonic vibration detection signal by an ultrasonic vibration detection system of which sensor is a PZT. FIG. 6C illustrates a voltage waveform of an ultrasonic vibration detection signal which was acquired by averaging the detection signals acquired 128 times using another ultrasonic vibration detection system of which sensor is a PS-FBG that is not disposed on a fiber ring laser (FRL). The dotted line in FIG. 6C indicates the voltage waveform of the ultrasonic vibration detection signal when averaging is not performed.

FIG. 6D illustrates a voltage waveform of an ultrasonic vibration detection signal that is acquired without performing averaging by the vibration detection apparatus 1, in which the PS-FBG is disposed on the FRL.

According to FIGS. 6A to 6D, it is confirmed that the ultrasonic vibration is detected at approximately the same arrival time regardless which of the following systems is used: the ultrasonic vibration detection system of which sensor is a PZT; the ultrasonic vibration detection system of which sensor is PS-FBG; and the vibration detection apparatus 1 in which the PS-FBG is disposed on the FRL.

It is also confirmed that the amplitude of the ultrasonic vibration detection signal detected by the vibration detection apparatus 1 is larger than the amplitude of the ultrasonic vibration detection signal detected by the ultrasonic vibration detection system, of which sensor is a PS-FBG or a PZT. This indicates that the sensitivity of the vibration detection apparatus 1 is higher than the sensitivity of the system of which sensor is a PS-FBG or a PZT. In other words, the vibration detection sensitivity can be improved by the transmitted light detection method which selects the main longitudinal mode using the PS-FBG having a sharp peak in the transmission spectrum and measures the amplitude.

Figure 7:
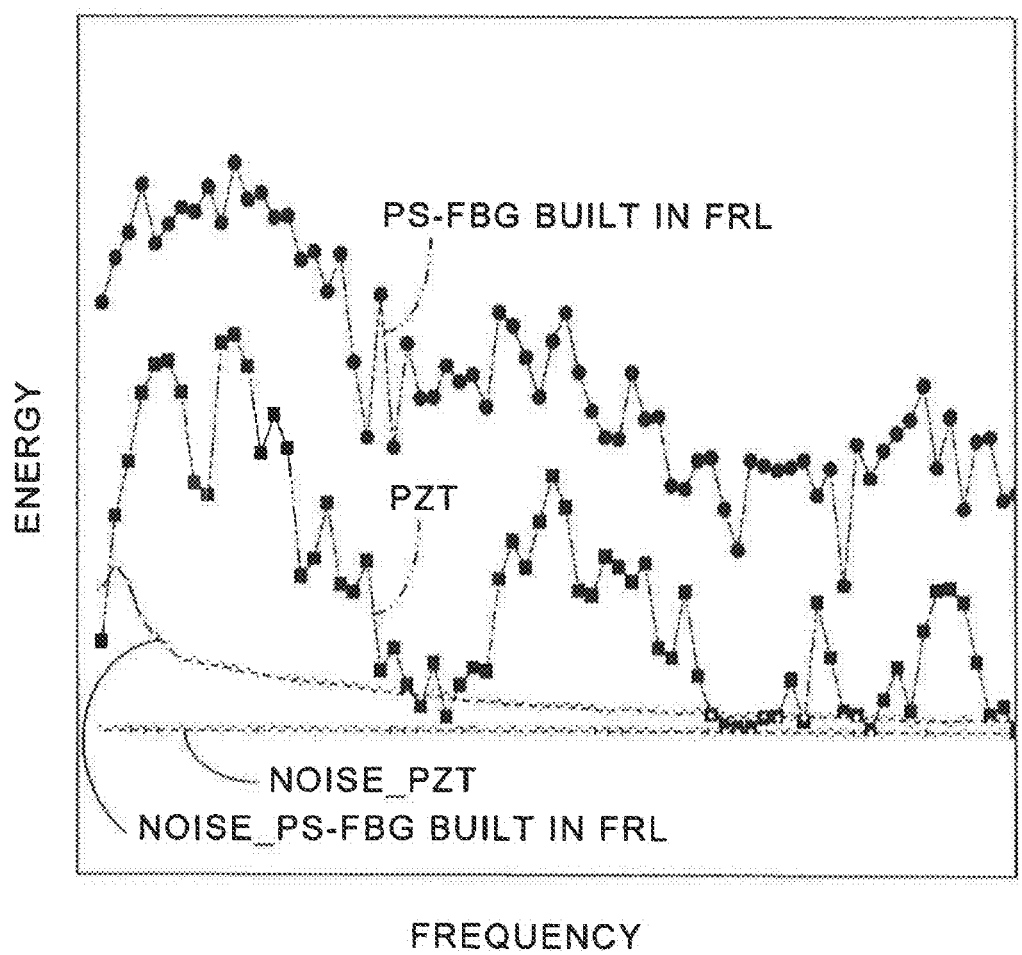
FIG. 7 is a diagram illustrating the comparison between the energy of a detection signal having different frequencies detected by the vibration detection apparatus in FIG. 1, and a result when a PZT sensor is used.

FIG. 7 is a diagram illustrating the comparison between the energy of a detection signal having different frequencies detected by the vibration detection apparatus 1 in FIG. 1, and a result when the PZT sensor is used.

In FIG. 7, the abscissa indicates the frequency of the detection signal, and the ordinate indicates the energy of the detection signal. In FIG. 7, a black dot indicates the energy of the detection signal of the vibration detection apparatus 1, a black square indicates the energy of the detection signal of the system using the PZT sensor, a white circle indicates the energy of the noise superimposed on the detection signal by the vibration detection apparatus 1, and a white square indicates the energy of the noise superimposed on the detection signal of the system using the PZT sensor.

As illustrated in FIG. 7, it is confirmed that when the ultrasonic vibration is detected as the detection signal using the vibration detection apparatus 1 in which the PS-FBG is disposed on the FRL, the energy of the noise component is larger than the case of using the PZT sensor-based system, but the energy of the detection signal is larger when the vibration detection apparatus 1 is used. Moreover, the energy of the ultrasonic vibration detection signal is higher at any frequency compared with the case of the system using the PZT sensor.

In particular, in the case of the system using the PZT sensor, the energy of the detection signal drops at certain frequencies, but in the case of the vibration detection apparatus 1 in which the PS-FBG is disposed on the FRL, the energy of the detection signal does not drop at any frequency.

Figure 8:
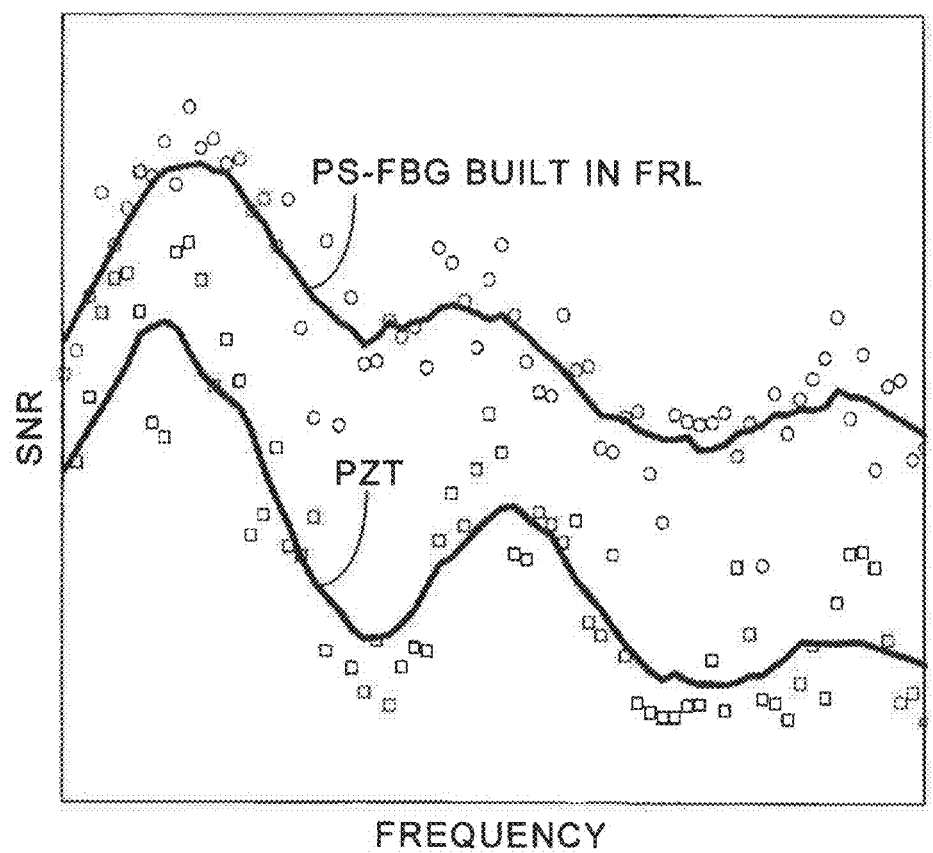
FIG. 8 is a diagram illustrating the comparison between the SNR of a detection signal having different frequencies detected by the vibration detection apparatus in FIG. 1, and a result when a PZT sensor is used.

FIG. 8 is a diagram illustrating the comparison between the SNR of a detection signal having different frequencies detected by the vibration detection apparatus 1 in FIG. 1, and a result when the PZT sensor is used.

In FIG. 8, the abscissa indicates the frequency of the detection signal, and the ordinate indicates the SNR of the detection signal. The white circle in FIG. 8 indicates the SNR of the detection signal of the vibration detection apparatus 1, the white square indicates the SNR of the detection signal of the system using the PZT sensor, and the two solid lines indicate the curves acquired by smoothing the plot data of each SNR respectively.

As illustrated in FIG. 8, it is confirmed that the SNR of the detection signal has a similar tendency as the energy of the detection signal. In other words, in the case of the vibration detection apparatus 1, the SNR of the ultrasonic vibration detection signal is higher at any frequency compared with the case of the system using the PZT sensor. Moreover, the frequency change of the SNR is smoother when the vibration detection apparatus 1 is used compared with the case of the system using the PZT sensor.

According to the results in FIG. 7 and FIG. 8, it is confirmed that the frequency response characteristic of the vibration detection apparatus 1 is better than the system using the PZT sensor.

In addition to these effects, the vibration detection apparatus 1 does not need such an expensive component as a tunable laser. Therefore the vibration of the object O can be detected by using an inexpensive configuration.

Further, if the PS-FBG is used as the FBG 6, and a specific longitudinal mode is selected from a plurality of longitudinal modes, then the influence of environmental changes, such as a temperature change, can be decreased. In other words, the vibration detection apparatus 1 becomes strongly resistant to environmental influences. In concrete terms, the laser mode of the transmitted light can be self-adjusted to a laser mode that has an appropriate wavelength.

As a result, a highly sensitive vibration measurement using the PS-FBG having a sharp peak in the transmission spectrum and a wide band of measurement range can be simultaneously implemented. This makes an adjustment responding to environmental changes, such as a temperature change, easier.

Although specific implementations have been described, the described implementations are merely examples, and do not limit the scope of the invention. New methods and apparatuses described here can be implemented in various other modes. In the modes of the methods and apparatuses described here, various omissions, replacements and changes can be performed within a scope that does not depart from the spirit of the invention. The appended Claims and equivalents thereof are included within the scope and summary of the invention, and include various modes and modifications thereof.

The invention claimed is:

1. A vibration detection apparatus, comprising:
a ring laser resonator that generates a laser beam propagating a ring-shaped light path;
a fiber Bragg grating which is disposed in the ring laser resonator such that the laser beam enters the grating, and of which transmittance distribution characteristic of transmitted light in a wavelength direction changes in accordance with vibration of an object; and
a detection system that detects the vibration based on the transmitted light through the fiber Bragg grating.

2. The vibration detection apparatus according to claim 1, wherein the fiber Bragg grating is constituted by a phase shift fiber Bragg grating.

3. The vibration detection apparatus according to claim 2, wherein the detection system is configured to detect the vibration based on a change of intensity of a longitudinal mode representing a highest intensity of light that is transmitted through the phase shift fiber Bragg grating, out of multiple longitudinal modes generated in the ring laser resonator.

4. The vibration detection apparatus according to claim 3, wherein the detection system is configured such that, when the transmittance distribution characteristic is shifted in the wavelength direction by a shift amount exceeding a threshold due to an environmental factor other than the vibration, the vibration is detected based on a change of intensity of another longitudinal mode corresponding to the shift amount.

5. The vibration detection apparatus according to claim 1, further comprising an optical filter that removes components in an unnecessary frequency band from the transmitted light through the fiber Bragg grating.

6. The vibration detection apparatus according to claim 5, wherein the optical filter is connected to the ring laser resonator via an optical circulator.

7. The vibration detection apparatus according to claim 5 wherein the optical filter is constituted by an apodized fiber Bragg grating.

8. The vibration detection apparatus according to claim 1, further comprising an optical amplifier that is disposed in the ring laser resonator, and that amplifies the transmitted light through the fiber Bragg grating and allows the light to enter the fiber Bragg grating again, wherein the detection system is configured to detect the vibration based on the transmitted light through the fiber Bragg grating, of which intensity has reached a predetermined intensity by amplifying the transmitted light by the optical amplifier at least once.

9. The vibration detection apparatus according to claim 1, further comprising an ultrasonic transmission system that applies vibration by an ultrasound wave to the object, wherein the detection system is configured to detect the vibration of the object generated by the ultrasound wave.

10. The vibration detection apparatus according to claim 1, wherein the detection system is configured to detect the vibration due to acoustic emissions generated in the object.

11. The vibration detection apparatus according to claim 1, wherein the detection system is configured to detect a defect in the object based on the detected vibration.

12. A vibration detection method, comprising the steps of:
generating a laser beam with a ring laser resonator and propagating the generated laser beam through a ring-shaped light path of the ring laser resonator;
allowing the laser beam to enter a fiber Bragg grating disposed in the ring laser generator such that the laser beam enters the grating, and of which transmittance distribution characteristic of transmitted light in a wavelength direction changes in accordance with vibration of an object; and
detecting the vibration based on the transmitted light through the fiber Bragg grating.

* * * * *